(12) United States Patent
Aikawa

(10) Patent No.: US 9,234,945 B2
(45) Date of Patent: Jan. 12, 2016

(54) DIFFERENTIAL TRANSFORMER TYPE MAGNETIC SENSOR AND IMAGE FORMING APPARATUS

(71) Applicant: KYOCERA DOCUMENT SOLUTIONS INC., Osaka (JP)

(72) Inventor: Yukihiro Aikawa, Osaka (JP)

(73) Assignee: KYOCERA Document Solutions Inc., Osaka (JP)

(*) Notice: Subject to any disclaimer, the term of this patent is extended or adjusted under 35 U.S.C. 154(b) by 127 days.

(21) Appl. No.: 14/045,686

(22) Filed: Oct. 3, 2013

(65) Prior Publication Data

US 2014/0097836 A1     Apr. 10, 2014

(30) Foreign Application Priority Data

Oct. 4, 2012   (JP) ................................ 2012-222001

(51) Int. Cl.
*G01R 33/02*   (2006.01)
*G01R 33/028*  (2006.01)
*G01R 33/04*   (2006.01)
(Continued)

(52) U.S. Cl.
CPC .............. *G01R 33/028* (2013.01); *G01R 33/04* (2013.01); *G03G 15/086* (2013.01); *G03G 15/0853* (2013.01); *A61B 17/00* (2013.01); *A61B 2217/00* (2013.01); *A61B 2218/00* (2013.01); *G03G 2215/00624* (2013.01)

(58) Field of Classification Search
CPC ...... A61B 1/00; A61B 17/00; A61B 2217/00; A61B 2218/00

USPC ......................................................... 324/258
See application file for complete search history.

(56) References Cited

U.S. PATENT DOCUMENTS

| 5,389,876 A | 2/1995 | Hedengren et al. |
| 6,429,651 B1 | 8/2002 | Choi et al. |
| 7,911,295 B2 | 3/2011 | Inuzuka et al. |

(Continued)

FOREIGN PATENT DOCUMENTS

| JP | H05-142205 A | 6/1993 |
| JP | 2001-099654 A | 4/2001 |

(Continued)

OTHER PUBLICATIONS

The extended European search report issued on Jan. 31, 2014, which corresponds to European Patent Application No. 13187060.2-1560 and is related to U.S. Appl. No. 14/045,686.

(Continued)

*Primary Examiner* — Huy Q Phan
*Assistant Examiner* — Temilade Rhodes-Vivour
(74) *Attorney, Agent, or Firm* — Studebaker & Brackett PC

(57) ABSTRACT

A differential transformer type magnetic sensor includes a first coil layer, a second coil layer, and an insulating layer formed between the first coil layer and the second coil layer. The first coil layer includes a detection coil and a first drive coil. The second coil layer includes a reference coil and a second drive coil. The first drive coil and the second drive coil are electrically connected together so that a direction of drive current flowing in the first drive coil is the same as a direction of drive current flowing in the second drive coil. The detection coil and the reference coil are electrically connected together so that a direction of induced current flowing in the detection coil is reverse to a direction of induced current flowing in the reference coil.

4 Claims, 11 Drawing Sheets

(51) Int. Cl.
*G03G 15/08* (2006.01)
*A61B 17/00* (2006.01)

(56) References Cited

U.S. PATENT DOCUMENTS

| | | | |
|---|---|---|---|
| 7,956,567 B2 | 6/2011 | Ryu | |
| 2003/0080733 A1* | 5/2003 | Miyata et al. | 324/207.17 |
| 2005/0238369 A1* | 10/2005 | Nakano | G03G 15/0856 399/27 |
| 2006/0127111 A1* | 6/2006 | Komori | G03G 15/0853 399/30 |
| 2008/0216589 A1* | 9/2008 | Shimizu | 73/862.333 |
| 2009/0003191 A1 | 1/2009 | Inuzuka et al. | |
| 2009/0058348 A1 | 3/2009 | Ryu | |
| 2010/0290795 A1* | 11/2010 | Seki | G03G 15/0853 399/30 |
| 2010/0308113 A1* | 12/2010 | Momose | G07D 7/04 235/450 |
| 2012/0274185 A1* | 11/2012 | Kanemitsu et al. | 310/68 B |

FOREIGN PATENT DOCUMENTS

| | | |
|---|---|---|
| JP | 2001-165910 A | 6/2001 |
| JP | 2001-185419 A | 7/2001 |
| JP | 2008-203064 A | 9/2008 |
| WO | 2006/121003 A1 | 11/2006 |

OTHER PUBLICATIONS

Choi S.O. et al.; "An integrated micro fluxgate magnetic sensor"; Sensors and Actuators A; Elsevier Sequoia S.A.; Jul. 1996; pp. 121-126; vol. 55, No. 2.

An Office Action; "Notice of Reasons for Rejection," issued by the Japanese Patent Office on Mar. 3, 2015, which corresponds to Japanese Patent Application No. 2012-222001 and is related to U.S. Appl. No. 14/045,686.

\* cited by examiner

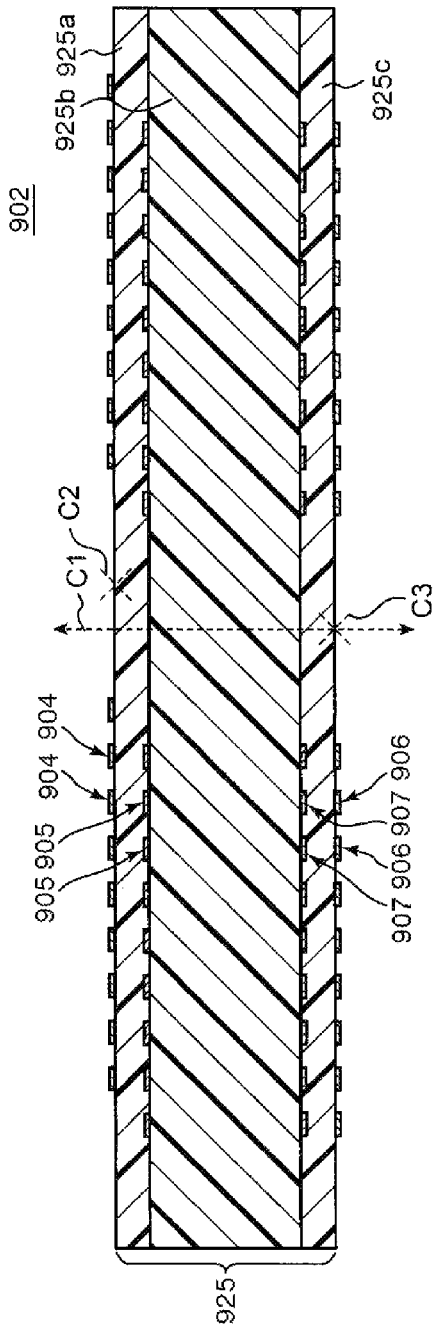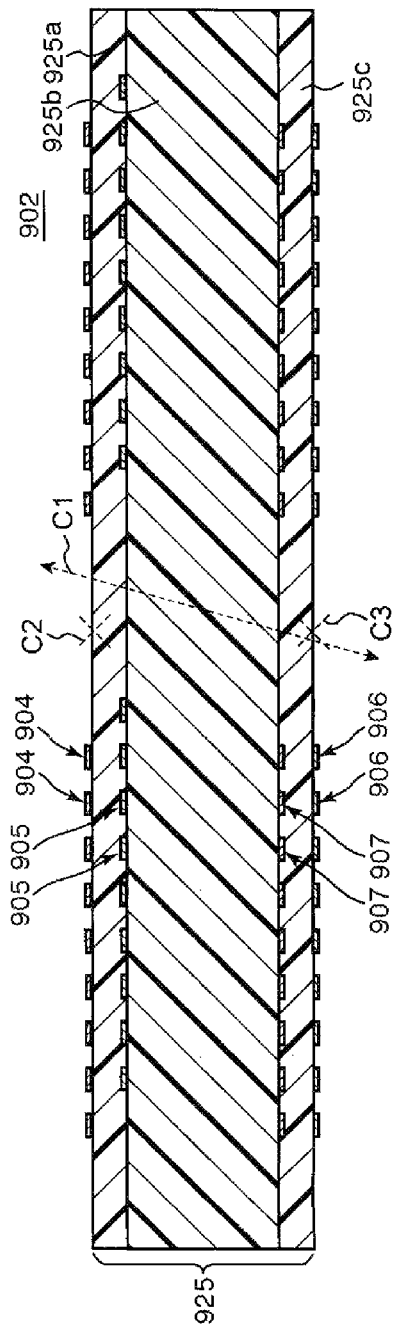
FIG. 7A
FIG. 7B

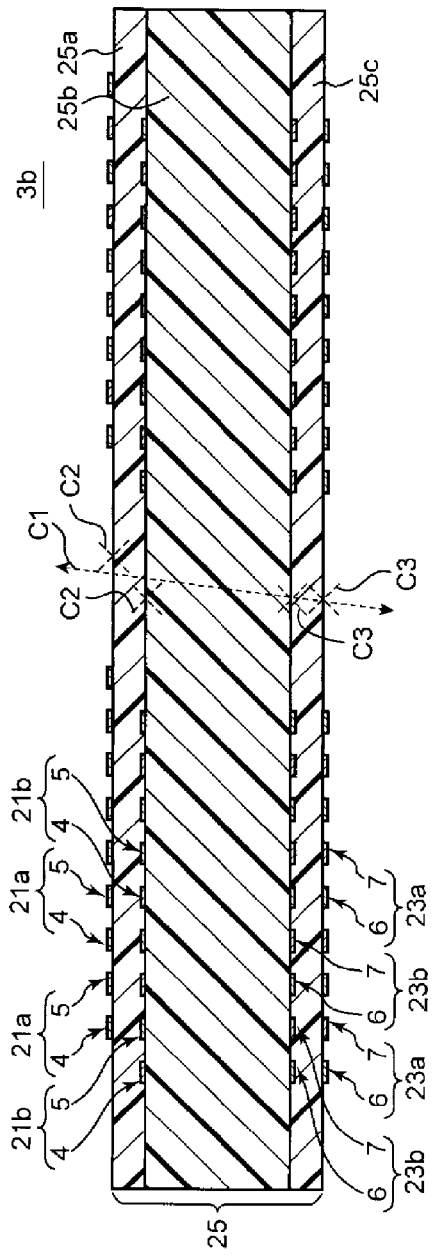
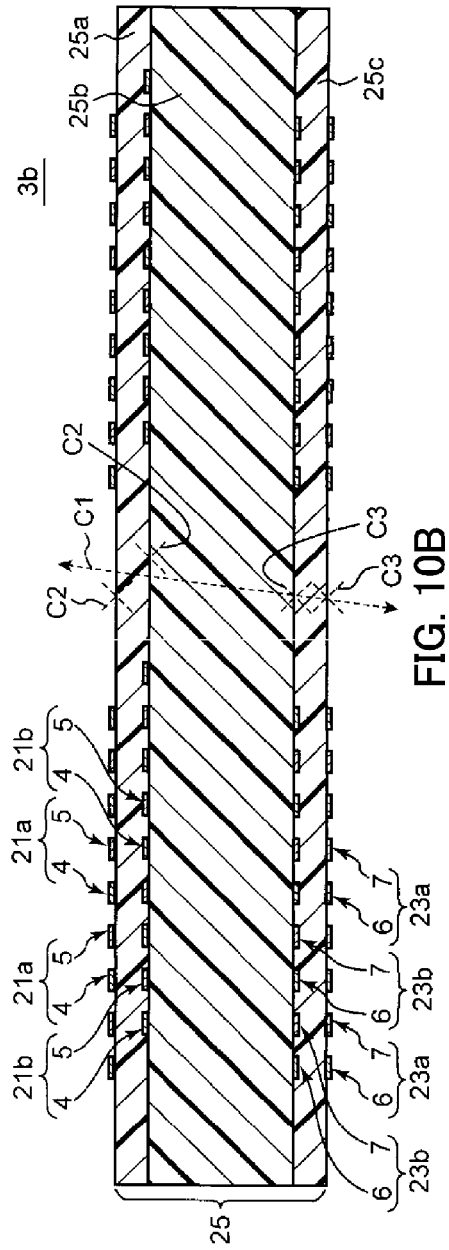

DIFFERENTIAL TRANSFORMER TYPE MAGNETIC SENSOR AND IMAGE FORMING APPARATUS

INCORPORATION BY REFERENCE

The present application claims priority under 35 U.S.C. §119 to Japanese Patent Application No. 2012-222001, filed Oct. 4, 2012. The contents of this application are incorporated herein by reference in their entirety.

BACKGROUND

The present disclosure relates to differential transformer type magnetic sensors and image forming apparatuses.

Image forming apparatuses using toner as developer exploit a magnetic sensor to detect the residual amount or density of the toner. Various types of magnetic sensors are proposed. A magnetic sensor of differential transformer type as one of the types has a configuration in which a drive coil, a detection coil, and a reference coil are arranged on the same core.

The use of planer coils as the coils can reduce the size of the differential transformer type magnetic sensor. As one example of the differential transformer type magnetic sensor using the planer coils, there has been proposed a sensor in which a first coil (drive coil), a second coil (reference coil), a third coil (detection coil), and a fourth coil (drive coil) are arranged in a first layer, a second layer, a third layer, and a fourth layer, respectively, and insulating substrates are disposed between the respective layers.

SUMMARY

A differential transformer type magnetic sensor according to the present disclosure includes a first coil layer, a second coil layer, and a first insulating layer. The first coil layer includes a detection coil formed of a planospiral first wire located on a plane and a first drive coil formed of a planospiral second wire running in parallel to the first wire on the same plane as the first wire. The second coil layer includes a reference coil formed of a planospiral third wire located on a plane and a second drive coil formed of a planospiral fourth wire running in parallel to the third wire on the same plane as the third wire. The first insulating layer is arranged between the first coil layer and the second coil layer. The first drive coil and the second drive coil are electrically connected together so that a direction of drive current flowing in the first drive coil is the same as a direction of drive current flowing in the second drive coil. The detection coil and the reference coil are electrically connected together so that a direction of induced current flowing in the detection coil is reverse to a direction of induced current flowing in the reference coil.

An image forming apparatus according to the present disclosure includes a differential transformer type magnetic sensor. The differential transformer type magnetic sensor includes a first coil layer, a second coil layer, and a first insulating layer. The first coil layer includes a detection coil formed of a planospiral first wire located on a plane and a first drive coil formed of a planospiral second wire running in parallel to the first wire on the same plane as the first wire. The second coil layer includes a reference coil formed of a planospiral third wire located on a plane and a second drive coil formed of a planospiral fourth wire running in parallel to the third wire on the same plane as the third wire. The first insulating layer is arranged between the first coil layer and the second coil layer. The first drive coil and the second drive coil are electrically connected together so that a direction of drive current flowing in the first drive coil is the same as a direction of drive current flowing in the second drive coil. The detection coil and the reference coil are electrically connected together so that a direction of induced current flowing in the detection coil is reverse to a direction of induced current flowing in the reference coil.

BRIEF DESCRIPTION OF THE DRAWINGS

FIG. 7A is a diagram showing an example of a cross section of the differential transformer type magnetic sensor according to Comparative Example in a state where a coil formed position is displaced.

FIG. 7B is a diagram showing an example of a cross section of the differential transformer type magnetic sensor according to Comparative Example in a state where a coil formed position is displaced.

FIG. 10A is diagram showing an example of a cross section of the differential transformer type magnetic sensor according to the second embodiment in a state where coil formed positions are displaced.

FIG. 10B is a diagram showing an example of a cross section of the differential transformer type magnetic sensor according to the second embodiment in a state where coil formed positions are displaced.

DETAILED DESCRIPTION

Figure 1:
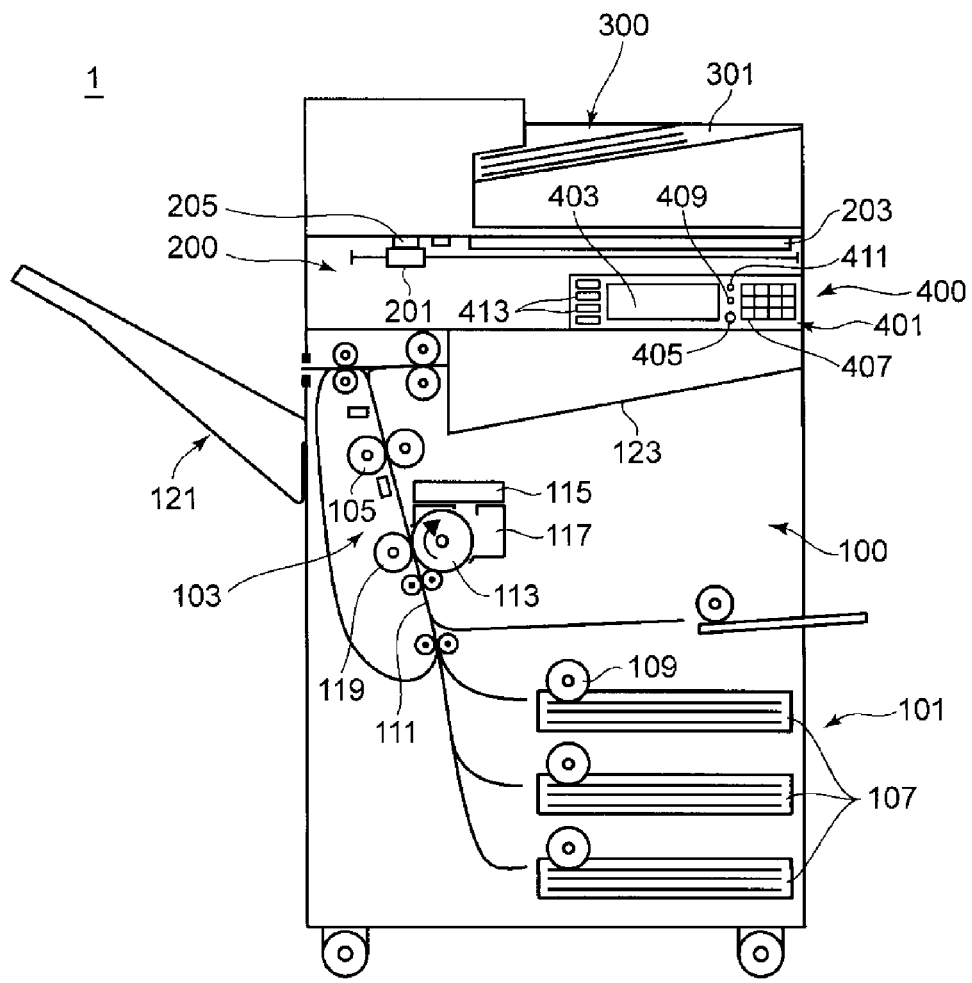
FIG. 1 is a diagram schematically showing an internal structure of an image forming apparatus to which a differential transformer type magnetic sensor according to one embodiment of the present disclosure can be applied.

Embodiments of the present disclosure will be described in detail below with reference to the accompanying drawings. FIG. 1 is a diagram schematically showing an internal structure of an image forming apparatus 1 to which a differential transformer type magnetic sensor according to one embodiment of the present disclosure can be applied. The image forming apparatus 1 is applicable to, for example, a digital multifunction peripheral having functions of a copier, a printer, a scanner, and a facsimile machine. The image forming apparatus 1 includes an apparatus main body 100, a document reading section 200 arranged on the apparatus main body 100, a document feed section 300 arranged on the document reading section 200, and an operation section 400 arranged in the front of the upper part of the apparatus main body 100.

The document feed section 300 functions as an automatic document feeder and can send a plurality of original documents placed on a document placement section 301 so that the document reading section 200 successively reads the original documents.

The document reading section 200 includes a carriage 201 on which an exposure lamp and the like are boarded, a document table 203 formed of a transparent member, such as glass or the like, a charge coupled device (CCD) sensor not shown, and a document reading slit 205. In reading an original document placed on the document table 203, the CCD sensor reads the original document, while the carriage 201 is moved in the longitudinal direction of the document table 203. By contrast, in reading an original document fed from the document feed section 300, the CCD sensor reads the original document sent from the document feed section 300 through the document reading slit 205, while the carriage 201 is moved to a site facing the document reading slit 205. The CCD sensor outputs the read original document as image data.

The apparatus main body 100 includes a paper storage section 101, an image forming section 103, and a fixing section 105. The paper storage section 101 is arranged at the lowermost part of the apparatus main body 100 and includes paper trays 107, each of which can store a sheaf to paper. The uppermost paper of the sheaf of paper stored in each paper tray 107 is sent toward a paper conveyance path 111 by driving a pickup roller 109. The paper is conveyed to the image forming section 103 through the paper conveyance path 111.

The image forming section 103 forms a toner image onto the conveyed paper. The image forming section 103 includes a photosensitive drum 113, an exposure section 115, a development section 117, and a transfer section 119. The exposure section 115 produces light correspondingly modified to image data (image data output from the document reading section 200, image data transmitted from a personal computer, image data received by the facsimile function, etc.) and irradiates the light to the uniformly and electrostatically charged peripheral surface of the photosensitive drum 113. Thus, an electrostatic latent image corresponding to the image data is formed on the peripheral surface of the photosensitive drum 113. When toner is supplied in this state from the development section 117 to the peripheral surface of the photosensitive drum 113, a toner image corresponding to the image data is formed on the peripheral surface. The transfer section 119 transfers this toner image to the paper conveyed from the aforementioned paper storage section 101.

The paper to which the toner image is transferred is sent to the fixing section 105. Heat and pressure are applied to the toner image and the paper in the fixing section 105, thereby fixing the toner image to the paper. The paper is ejected onto a stacking tray 121 or an exit tray 123. Thus, the image forming apparatus 1 prints a monochrome image.

The operation section 400 includes an operation key section 401 and a display section 403. The display section 403 has a function of a touch panel to display a screen including soft keys. The user manipulates the soft keys, while watching the screen, to perform setting necessary for execution of the copying function or the like.

The operation key section 401 includes operation keys of hard keys. Specifically, the operation key section 401 includes a start key 405, a numeric keypad 407, a stop key 409, a reset key 411, a function switch key 413 for switch among the copy function, the print function, the scan function, and the facsimile function, etc.

The start key 405 is a key to start an operation of copying, facsimile transmission, etc. The numeric keypad 407 includes keys to input a numeral of the number of copies, facsimile numbers, etc. The stop key 409 is a key to stop the copying operation or the like in middle. The reset key 411 is a key to return the currently set content to the initial state.

The function switch key 413 includes a copy key, a transmission key, etc. to switch among the copying function, the transmission function, etc. Manipulation of the copy key results in display of an initial screen for copy on the display section 403. Manipulation of the transmission key results in display of an initial screen for facsimile transmission and mail transmission on the display section 403.

Figure 2:
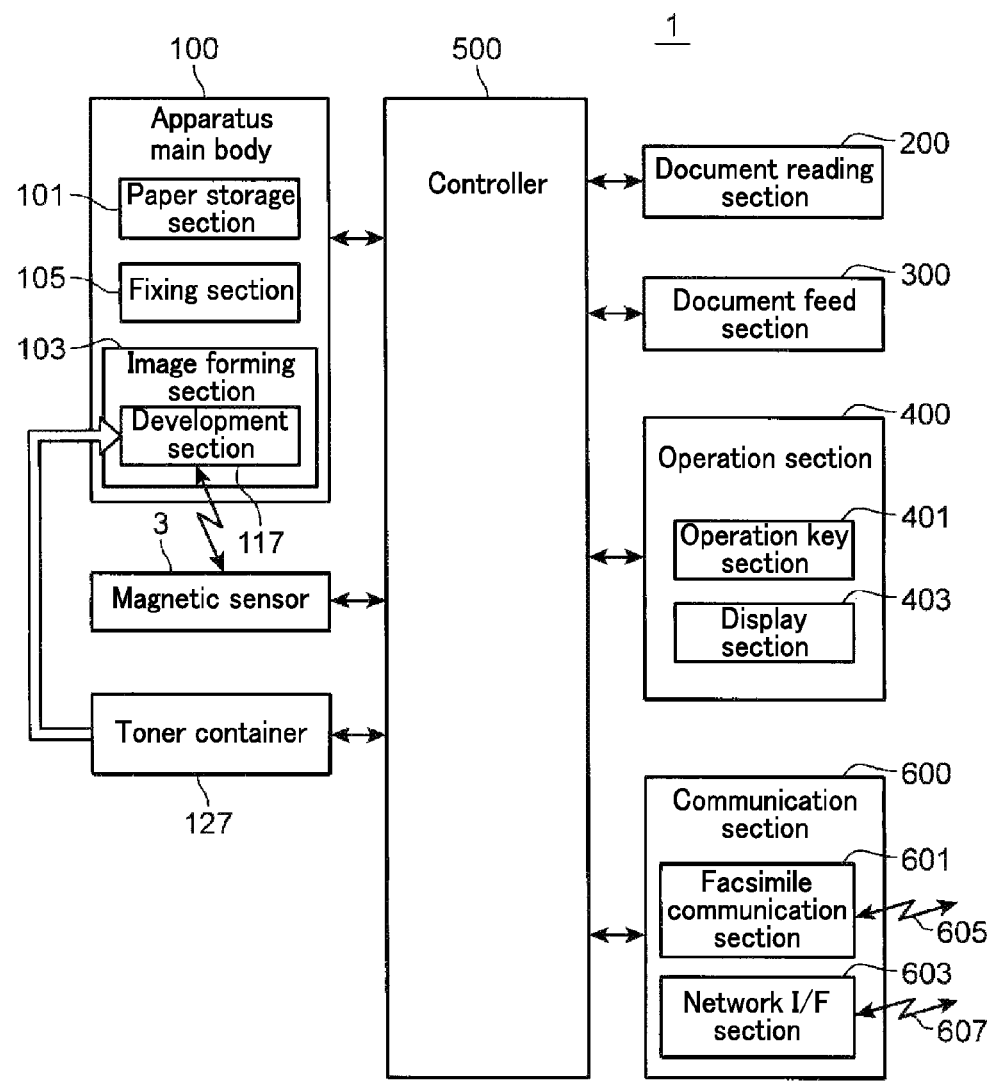
FIG. 2 is a block diagram showing a configuration of the image forming apparatus shown in FIG. 1.

FIG. 2 is a block diagram showing a configuration of the image forming apparatus 1 shown in FIG. 1. The image forming apparatus 1 has a configuration in which the apparatus main body 100, a differential transformer type magnetic sensor 3, a toner container 127, the document reading section 200, the document feed section 300, the operation section 400, a controller 500, and a communication section 600 are connected together through a bus. Description has been made about the apparatus main body 100, the document reading section 200, the document feed section 300, and the operation section 400 as above. Therefore, duplicate description is omitted.

The toner container 127 accommodates the toner (magnetized mono-component developer). The toner is replenished from the toner container 127 to the development section 117.

The differential transformer type magnetic sensor 3 detects variation in height of the toner in the development section 117. The residual amount of the toner in the development section 117 is measured on the basis of the detection. The differential transformer type magnetic sensor 3 will be described later in detail.

The controller 500 includes a central processing unit (CPU), a read only memory (ROM), a random access memory (RAM), an image memory, etc. The CPU performs control necessary for operation of the image forming apparatus 1 on the aforementioned respective elements of the image forming apparatus 1, such as the apparatus main body 100, etc. The ROM stores software necessary for control of the operation of the image forming apparatus 1. The RAM is exploited for temporary storage of data generated in execution of the software, storage of application software, etc. The image memory temporarily stores image data (image data output from the document reading section 200, image data transmitted from a personal computer, image data received by the facsimile function, etc.).

The communication section 600 includes a facsimile communication section 601 and a network I/F section 603. The facsimile communication section 601 includes a network control unit (NCU) to control connection of a telephone line 605 to a target facsimile machine and a modulation-demodulation circuit to modulate/demodulate signals for facsimile communication. The facsimile communication section 601 is connected to the telephone line 605.

The network I/F section 603 is connected to a local area network (LAN) 607. The network I/F section 603 is a communication interface circuit for execution of communication with a terminal device, such as a personal computer or the like connected to the LAN 607.

Figure 3:
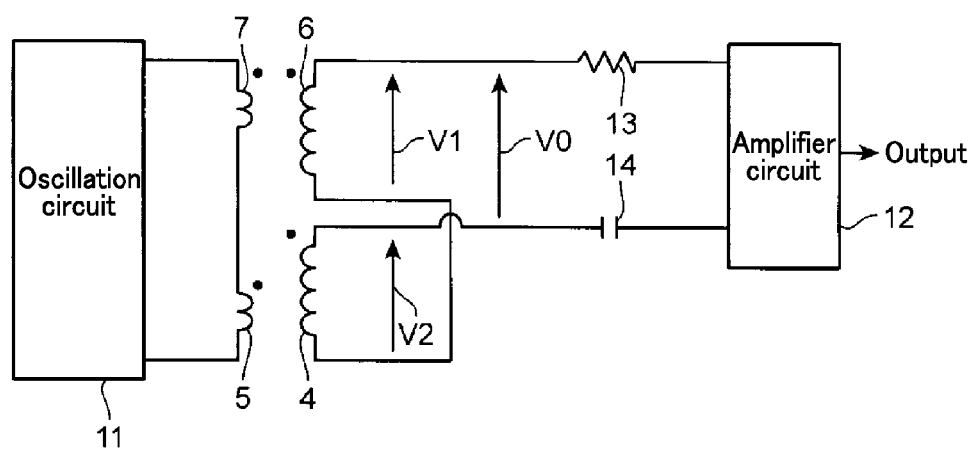
FIG. 3 is a diagram showing one example of a circuit diagram of a differential transformer type magnetic sensor.

FIG. 3 is a diagram showing one example of a circuit diagram of the differential transformer type magnetic sensor 3 (hereinafter it may be referred to as a magnetic sensor 3). The differential transformer type magnetic sensor 3 includes a detection coil 4, a first drive coil 5, a reference coil 6, a second drive coil 7, an oscillation circuit 11, an amplifier circuit 12, a resistor 13, and a capacitor 14.

The oscillation circuit 11 generates high frequency drive current to drive the first drive coil 5 and the second drive coil 7. The first drive coil 5 is connected in series to the second drive coil 7. One end of the first drive coil 5 is connected to one end of the second drive coil 7 so that the direction of a magnetic flux generated in the first drive coil 5 is the same as the direction of a magnetic flux generated in the second drive coil 77, in other words, so that the direction of the drive current flowing in the first drive coil 5 is the same as the direction of the drive current flowing in the second drive coil 7, when the drive current flows in the first drive coil 5 and the second drive coil. With this configuration, the magnetic flux generated in the first drive coil 5 and the magnetic flux generated in the second drive coil 7 may not cancel each other. The other end of the first drive coil 5 and the other end of the second drive coil 7 are connected to the oscillation circuit 11.

The detection coil 4 is magnetically coupled to the first drive coil 5. The reference coil 6 is magnetically coupled to the second drive coil 7. One end of the detection coil 4 is in differential connection in series to one end of the reference coil 6. In other words, the detection coil 4 and the reference coil 6 are electrically connected together so that directions of induced current flowing in the detection coil 4 and the reference coil 6 are reverse to each other. This cause differential voltage V0 (=electromotive force V1 of the reference coil 6 minus electromotive force V2 of the detection coil 4) to be input to the amplifier circuit 12.

The other end of the detection coil 4 is connected to the amplifier circuit 12 via the capacitor 14. The other end of the reference coil 6 is connected to the amplifier circuit 12 via the resistor 13. The resistor 13 is connected to the base of a bipolar transistor in the amplifier circuit 12 to be used for setting the amplification factor of the amplifier circuit 12.

The capacitor 14 has a function of cutting a DC component in the differential voltage V0. Thus, only an AC component in the differential voltage V0 is input to the amplifier circuit 12.

An operation of the magnetic sensor 3 will be briefly described. When the drive current generated in the oscillation circuit 11 flows in the first drive coil 5 and the second drive coil 7, the electromotive force V1 and the electromotive force V2 are caused in the reference coil 6 and the detection coil 4, respectively. The presence of the toner in the vicinity of the detection coil 4 makes the electromotive force V2 larger than the electromotive force V1. This means that the differential voltage V0 will not be 0 V. The amplifier circuit 12 amplifies the differential voltage V0. The residual amount of the toner is detected using signals output from the amplifier circuit 12.

Figure 4:
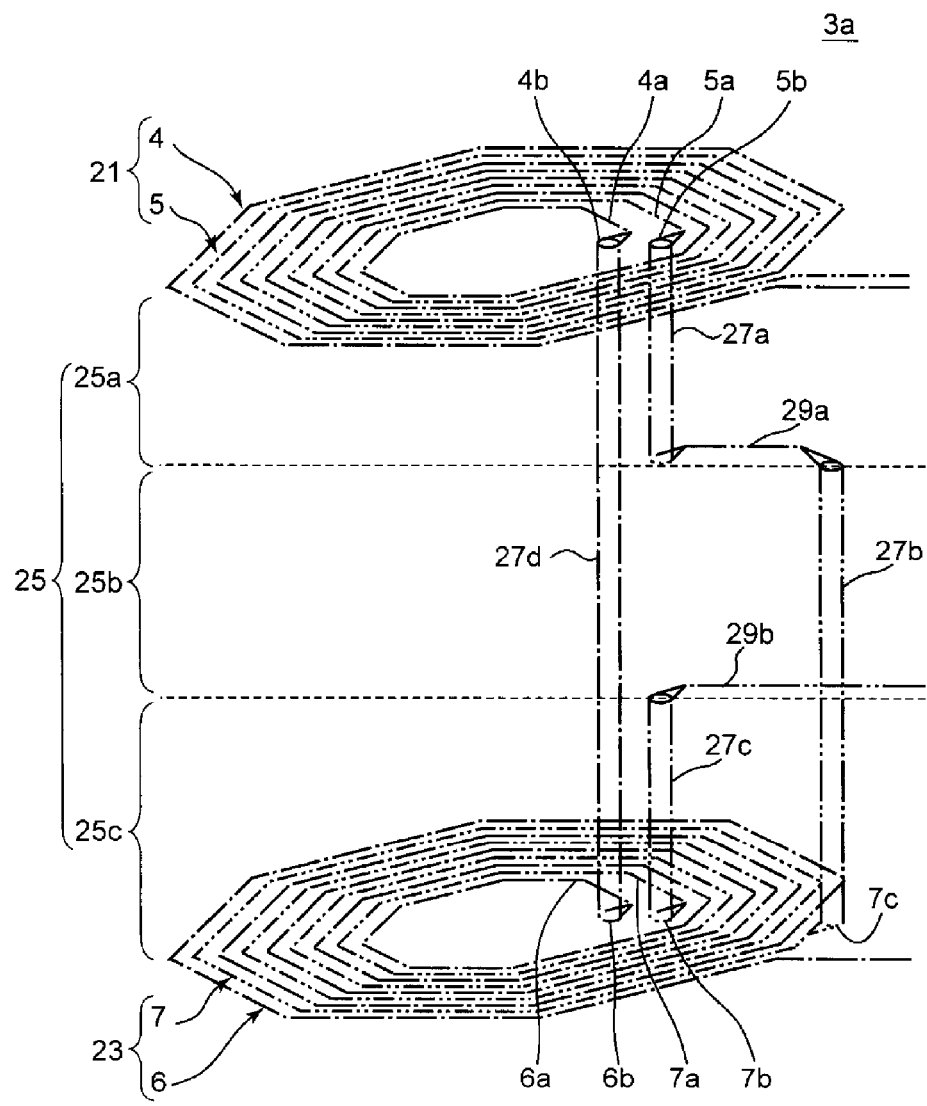
FIG. 4 is a perspective view showing a configuration of a differential transformer type magnetic sensor according to the first embodiment of the present disclosure.
Figure 5:
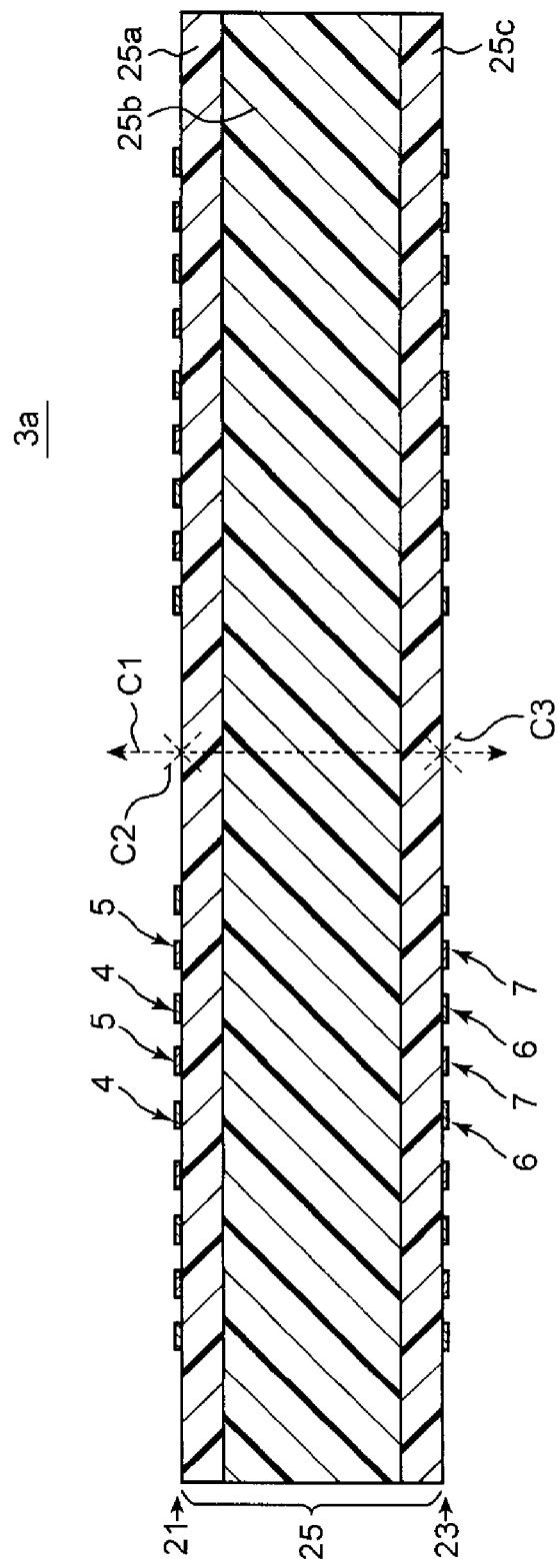
FIG. 5 is a cross sectional view of the differential transformer type magnetic sensor according to the first embodiment of the present disclosure.
Figure 8:
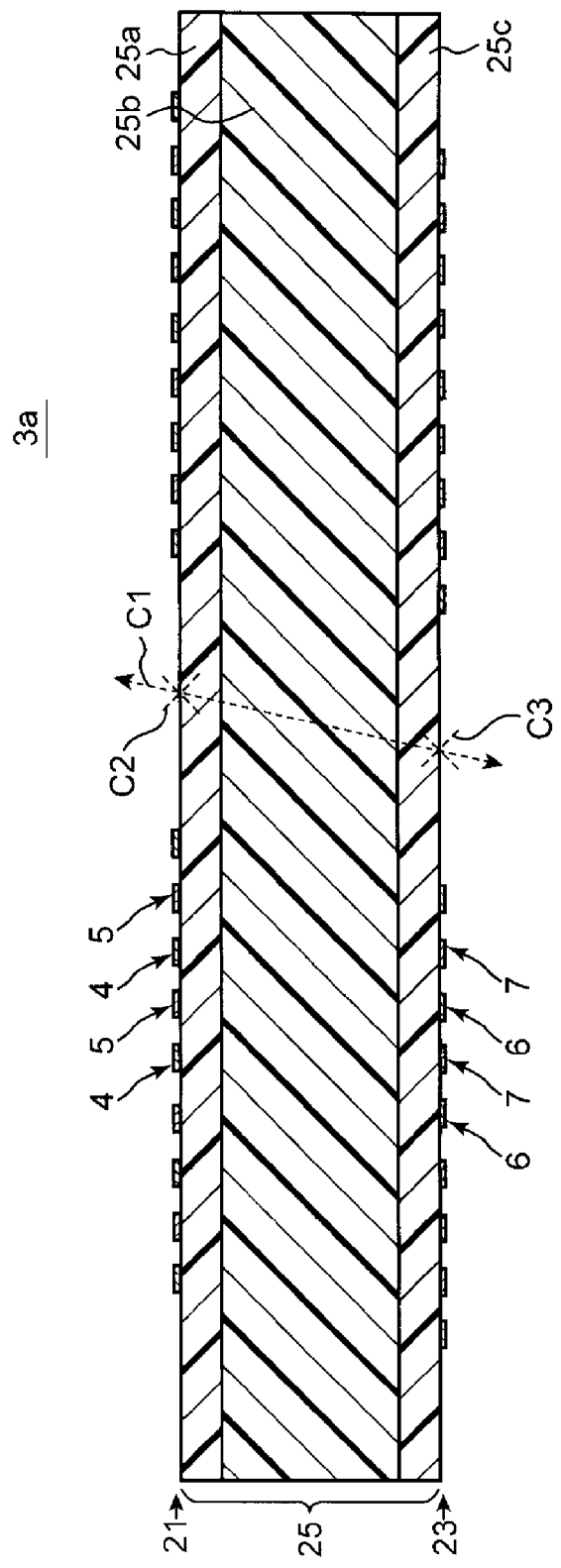
FIG. 8 is a diagram showing an example of a cross section of the differential transformer type magnetic sensor according to the first embodiment in a state where coil formed positions are displaced.

With reference to FIGS. 4, 5, and 8, description will be made next about a differential transformer type magnetic sensor 3a (hereinafter it may be referred to as a magnetic sensor 3a) according to the first embodiment of the present disclosure, which is applicable as the magnetic sensor 3. FIG. 4 is a perspective view showing a configuration of the magnetic sensor 3a. FIG. 5 is a cross sectional view of the magnetic sensor 3a.

The magnetic sensor 3a includes a first coil layer 21, a second coil layer 23, and a first insulating layer 25.

The first coil layer 21 is formed of a first wire 4a and a second wire 5a. The first wire 4a and the second wire 5a are arranged on the same plane (on the surface of an upper insulating film 25a) and are parallelly wound in the same direction in a spiral manner. That is, the first wire 4a and the second wire 5a are wound in a double spiral manner.

The first wire 4a is patterned so that the radius of the spiral with a terminal 4b as a start point increases in the anticlockwise direction when viewing the first coil layer 21 of the magnetic sensor 3a from above. The first wire 4a forms the detection coil 4 as a planer coil.

The second wire 5a is patterned so that the radius of the spiral with a terminal 5b as a start point increases in the anticlockwise direction when viewing the first coil layer 21 of the magnetic sensor 3a from above. The second wire 5a forms the first drive coil 5 as a planer coil.

The second coil layer 23 is formed of a third wire 6a and a fourth wire 7a. The third wire 6a and the fourth wire 7a are arranged on the same plane (on the surface of a lower insulating film 25c) and are parallelly wound in the same direction in a spiral manner. That is, the third wire 6a and the fourth wire 7a are wound in a double spiral manner.

The third wire 6a is patterned so that the radius of the spiral with a terminal 6b as a start point increases in the anticlockwise direction when viewing from the side of the first coil layer 21 of the magnetic sensor 3a. The third wire 6a forms the reference coil 6 as a planer coil.

The fourth wire 7a is patterned so that the radius of the spiral with a terminal 7b as a start point to reach a terminal 7c increases in the anticlockwise direction as an end point when viewing from the side of the first coil layer 21 of the magnetic sensor 3a. The fourth wire 7a forms the second drive coil 7 as a planer coil.

The insulating layer 25 is arranged between the first coil layer 21 and the second coil layer 23. The insulating layer 25 includes the upper insulating film 25a, an intermediate insulating film 25b, and the lower insulating film 25c.

The first coil layer 21 is formed on the surface of the upper insulating film 25a. The second coil layer 23 is formed on the surface of the lower insulating film 25c. The intermediate insulating film 25b is formed between the upper insulating film 25a and the lower insulating film 25c. In the first embodiment, the insulating layer 25 functions as a first insulating layer.

The first drive coil 5 and the second drive coil 7 are electrically connected together so that the direction of the drive current flowing in the first drive coil 5 is the same as the direction of the drive current flowing in the second drive coil 7. In order to achieve this configuration, the terminal 5b of the first drive coil 5 is electrically connected to the terminal 7c of the second drive coil 7.

Specifically, a connection plug 27a is formed to pass through the upper insulating film 25a. A connection plug 27b is formed to pass through the intermediate insulating film 25b and the lower insulating film 25c. A connection plug 27c is formed to pass through the lower insulating film 25c.

The terminal 5b of the first drive coil 5 is electrically connected to the connection plug 27a. The terminal 7c of the second drive coil 7 is electrically connected to the connection plug 27b. The connection plug 27a is connected to the terminal 5b located in the interior of the first drive coil 5. The connection plug 27b is connected to the terminal 7c located in the exterior of the second drive coil 7. The connection plug 27a extends in the normal direction of the surface of the upper insulating film 25a. The connection plug 27b extends in the normal direction of the surface of the lower insulating film 25c. Accordingly, the connection plug 27a cannot be directly connected to the connection plug 27b. As such, the connection plug 27a and the connection plug 27b are electrically connected together through a wiring 29a formed on the intermediate insulating film 25b.

The terminal 7b of the second drive coil 7 is located in the interior of the second drive coil 7. Accordingly, no wiring can be provided in the second coil layer 23 for connection of the terminal 7b to an external element for the second drive coil 7. As such, a wiring 29b is formed on the lower insulating film 25c and is electrically connected to the terminal 7b through the connection plug 27c.

The detection coil 4 and the reference coil 6 are electrically connected together so that the direction of the induced current flowing in the detection coil 4 is reverse to the direction of the induced current flowing in the reference coil 6. In order to achieve this configuration, the terminal 4b of the detection coil 4 and the terminal 6b of the reference coil 6 are electrically connected together through a connection plug 27d formed to pass through the insulating layer 25.

As shown in FIG. 5, where no displacement of formed positions of the detection coil 4, the first drive coil 5, the reference coil 6, and the second drive coil 7 is caused, a center C2 of the detection coil 4 and a center C3 of the reference coil 6 are located on a central axis C1 of the magnetic flux generated by flow of the drive current in the first drive coil 5 and the second drive coil 7.

The first wire 4a, the second wire 5a, the third wire 6a, and the fourth wire 7a are wound in the same direction in a spiral manner in the magnetic sensor 3a according to the first embodiment. However, the direction in which the third wire 6a and the fourth wire 7a are wound may be reverse to the direction in which the first wire 4a and the second wire 5a are wound. The reason for this is as follows. Even in such a configuration, by changing the connection between the first drive coil 5 and the second drive coil 7, the direction of the drive current flowing in the first drive coil 5 can be set to be the same as the direction of the drive current flowing in the second drive coil 7. Also, by changing the connection between the detection coil 4 and the reference coil 6, the direction of the induced current flowing in the detection coil 4 can be set to be reverse to the direction of the induced current flowing in the reference coil 6.

Figure 6:
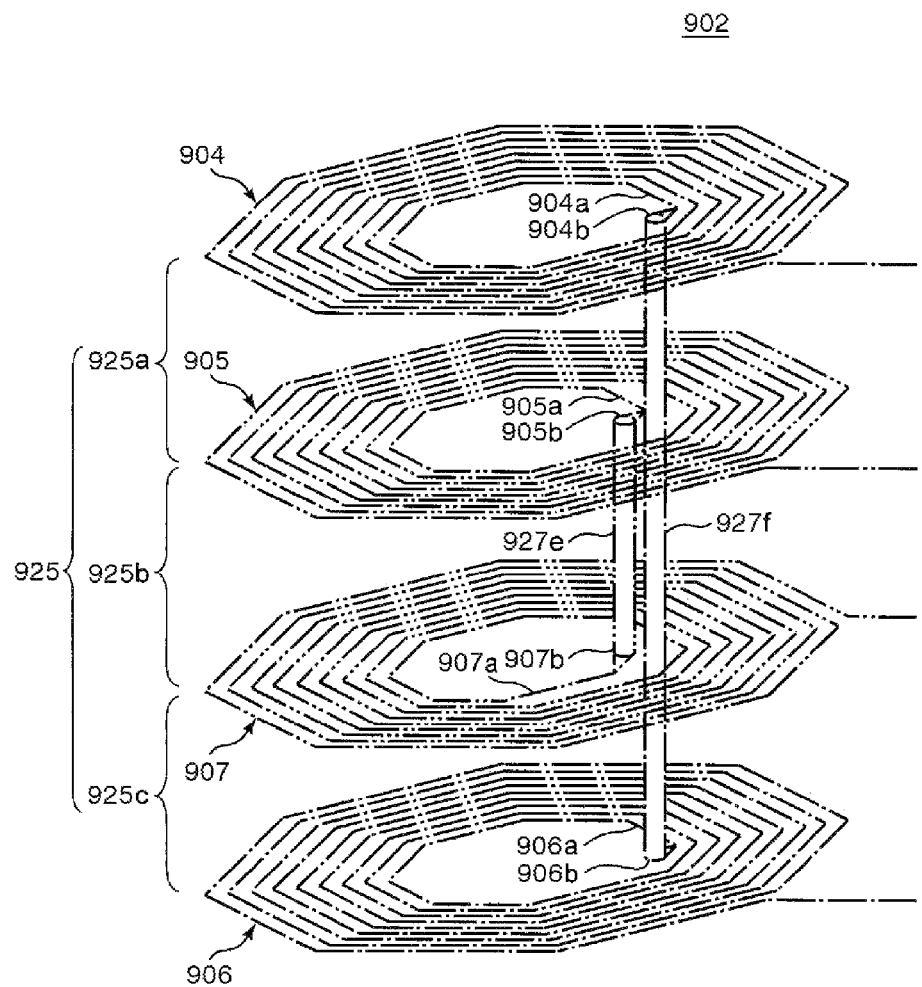
FIG. 6 is a perspective view showing a configuration of a differential transformer type magnetic sensor according to Comparative Example.

With reference to FIGS. 6, 7A, and 7B, advantages of the differential transformer type magnetic sensor 3a according to the first embodiment will be described in comparison with a differential transformer type magnetic sensor 902 according to Comparative Example. The same reference numbers as those for the elements that form the differential transformer type magnetic sensor 3a according to the first embodiment are used for corresponding elements of elements that form the differential transformer type magnetic sensor 902 according to Comparative Example, except the numbers of hundreds.

FIG. 6 is a perspective view showing a configuration of the differential transformer type magnetic sensor 902 according to Comparative Example. A first drive coil 905 of the magnetic sensor 902 in Comparative Example is formed between an upper insulating film 925a and an intermediate insulating film 925b. A second drive coil 907 is formed between the intermediate insulating film 925b and a lower insulating film 925c. That is, the first drive coil 905 is formed in a layer different from a layer in which a detection coil 904 is formed. The second drive coil 907 is formed in a layer different from a layer in which a reference coil 906 is formed.

A terminal 905b of the first drive coil 905 and a terminal 907b of the second drive coil 907 are electrically connected together through a connection plug 927e formed to pass through the intermediate insulating film 925b. This makes the direction of the drive current flowing in the first drive coil 905 to be the same as the direction of the drive current flowing in the second drive coil 907.

A terminal 904b of the detection coil 904 and a terminal 906b of the reference coil 906 are electrically connected together through a connection plug 927f formed to pass through the insulating layer 925. This makes the direction of the induced current flowing in the detection coil 904 to be reverse to the direction of the induced current flowing in the reference coil 906.

FIGS. 7A and 7B are diagram showing examples of cross sections of the differential transformer type magnetic sensor 902 according to Comparative Example shown in FIG. 6 in states where coil formed positions are displaced. FIG. 7A shows an example where the formed position of the detection coil 904 is displaced. FIG. 7B shows an example where the formed position of the first drive coil 905 is displaced.

Where displacement of the formed position of the detection coil 904 or the first drive coil 905 is caused, the amount of the magnetic flux passing through the detection coil 904 is smaller than the amount of the magnetic flux passing through the reference coil 906 in the absence of toner (magnetic material) as a detection target. As a result, the amount of the magnetic flux passing through the detection coil 904 is not equal to the amount of the magnetic flux passing through the reference coil 906. In other words, in the absence of the toner as a detection target, the induced current flowing in the detection coil 904 is smaller than the induced current flowing in the reference coil 906. As a result, the induced current flowing in the detection coil 904 is not equal to the induced current flowing in the reference coil 906. Where the amount of displacement of the formed position of any coil is different among a plurality of the magnetic sensors 902, dispersion of the difference may be caused between the amount of the magnetic flux passing through the detection coil 904 and the amount of the magnetic flux passing through the reference coil 906. This means different outputs among the magnetic sensors 902. For this reason, measurement accuracy decreases.

FIG. 8 is a diagram showing an example of a cross section of the magnetic sensor 3a according to the first embodiment in a state where coil formed positions are displaced. FIG. 5 is a diagram showing an example of a cross section of the magnetic sensor 3a according to the first embodiment in which no coil formed position is displaced, as has been already described. As understood from comparison between FIGS. 5 and 8, the formed positions of the detection coil 4 and the first drive coil 5 are displaced in FIG. 8.

As described above, the detection coil 4 and the first drive coil 5 are included in the first coil layer 21 and are formed in the same layer in the differential transformer type magnetic sensor 3a according to the first embodiment. For this reason, where the formed position of the detection coil 4 is displaced in forming the detection coil 4 and the first drive coil 5, the formed position of the first drive coil 5 is displaced by the same amount. As well, where the formed position of the first drive coil 5 is displaced, the formed position of the detection coil 4 is displaced by the same amount. Thus, no variation is caused in the relative positional relationship between the detection coil 4 and the first drive coil 5. Accordingly, even if the formed positions of the detection coil 4 and the first drive coil 5 are displaced, the amount of the magnetic flux passing through the detection coil 4 will not vary in the absence of the detection target.

Likewise, the reference coil 6 and the second drive coil 7 are included in the second coil layer 23 and are formed in the same layer. For this reason, where the formed position of the reference coil 6 is displaced in forming the reference coil 6 and the second drive coil 7, the formed position of the second drive coil 7 is displaced by the same amount. As well, where the formed position of the second drive coil 7 is displaced, the formed position of the reference coil 6 is displaced by the same amount. Thus, no variation is caused in the relative positional relationship between the reference coil 6 and the second drive coil 7. Accordingly, even if the formed positions of the reference coil 6 and the second drive coil 7 are displaced, the amount of the magnetic flux passing through the reference coil 6 will not vary in the absence of the detection target.

As described above, according to the first embodiment, even if the formed position of any of the detection coil 4, the first drive coil 5, the reference coil 6, and the second drive coil 7, which are planer coils, is displaced, the amount of the magnetic flux passing through the detection coil 4 and the amount of the magnetic flux passing through the reference coil 6 will not vary in the absence of the detection target. Accordingly, in the absence of the detection target, it can be prevented that the difference between the amount of the magnetic flux passing through the detection coil 4 and the amount of the magnetic flux passing through the reference coil 6 is different among a plurality of the differential transformer type magnetic sensors 3a. Thus, magnitude dispersion in the outputs of the differential transformer type magnetic sensors 3a can be reduced.

Figure 9:
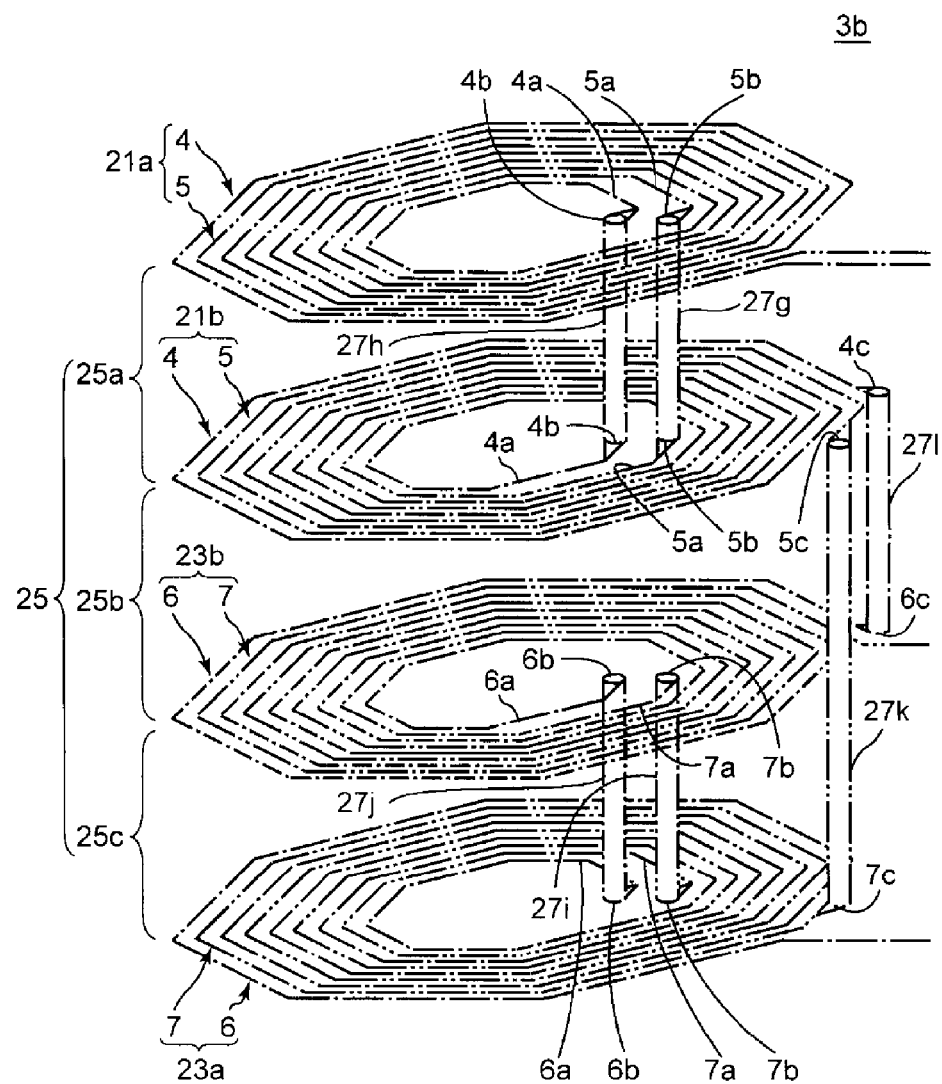
FIG. 9 is a perspective view showing a configuration of a differential transformer type magnetic sensor according to the second embodiment of the present disclosure.

With reference to FIGS. 9 and 10, a differential transformer type magnetic sensor 3b (hereinafter it may be referred to as a magnetic sensor 3b) according to the second embodiment will be described. The description will be made mainly about difference from the differential transformer type magnetic sensor 3a according to the first embodiment. In the first embodiment, each number of the first coil layer 21 and the second coil layer is one. While in the second embodiment, two first coil layers 21 and two second coil layers 23 are formed.

It is noted that although the example described herein is about a configuration in which the two first coil layers 21 and the two second coil layers 23 are formed, the second embodiment is applicable to the case where the numbers of the first coil layers 21 and the second coil layers 23 are any integers larger than two. In this case, a plurality of the first coil layers 21 are stacked alternately with insulating layers (second insulating layers). The insulating layers (second insulating layers) are interposed between two first coil layers 21 of the plurality of first coil layers. Also, the plurality of the second coil layers 23 are stacked alternately with insulating layers (third insulating layers). The insulating layers (third insulating layers) are interposed between two second coil layers 23 of the plurality of the second coil layers 23. Further, the number of the first coil layers 21 is preferably plural and equal to the number of the second coil layers 23. It is noted that the same reference numbers as those for the elements that form the magnetic sensor 3a according to the first embodiment are used for corresponding elements of elements that form the magnetic sensor 3b according to the second embodiment herein.

FIG. 9 is a perspective view showing a configuration of the magnetic sensor 3b. Each of a first coil layer 21a and a first coil layer 21b includes a detection coil 4 and a first drive coil 5. Each of a second coil layer 23a and a second coil layer 23b includes a reference coil 6 and a second drive coil 7.

The first coil layer 21a is formed on the upper surface of an upper insulating film 25a. The first coil layer 21b is formed between the upper insulating film 25a and an intermediate insulating film 25b. The second coil layer 23b is formed between the intermediate insulating film 25b and a lower insulating film 25c. The second coil layer 23a is formed on the lower surface of the lower insulating film 25c (i.e., the surface opposite to the surface on which the second coil layer 23b is formed out of the surfaces of the lower insulating film 25c).

In light of the upper insulating film 25a and the lower insulating film 25c, the upper insulating film 25a is formed between the first coil layer 21a and the first coil layer 21b (the upper insulating film 25a is stacked so as to be interposed between the first coil layers 21a and 21b on one of the surfaces of the intermediate insulating film 25b). The lower insulating film 25c is formed between the second coil layer 23a and the second coil layer 23b (the lower insulating film 25c is stacked so as to be interposed between the second coil layers 23a and 23b on the other surface of the intermediate insulating film 25b). In the second embodiment, the intermediate insulating film 25b functions as a first insulating layer. The upper insulating film 25a functions as a second insulating layer. The lower insulating film 25c functions as a third insulting layer.

The first coil layer 21a, the upper insulating film 25a, the first coil layer 21b, the intermediate insulating film 25b, the second coil layer 23b, the lower insulating film 25c, and the second coil layer 23a are stacked in this order in the magnetic sensor 3b.

Difference between the first coil layer 21a and the first coil layer 21b lies in the winding directions of the wires. In the first coil layer 21a, the first wire 4a is patterned so that the radius of the spiral with a terminal 4b as a start point increases in the anticlockwise direction when viewing the first coil layer 21a of the magnetic sensor 3b from above. The first wire 4a forms the detection coil 4 as a planer coil. The second wire 5a is patterned so that the radius of the spiral with a terminal 5b as a start point increases in the anticlockwise direction when viewing the first coil layer 21a of the magnetic sensor 3b from above. The second wire 5a forms the first drive coil 5 as a planer coil.

On the other hand, in the first coil layer 21b, the first wire 4a is patterned so that the radius of the spiral with a terminal 4b as a start point increases in the clockwise direction when viewing from the side of the first coil layer 21a of the magnetic sensor 3b. The first wire 4a forms the detection coil 4 as a planer coil. The second wire 5a is patterned so that the radius of the spiral with a terminal 5b as a start point increases in the clockwise direction when viewing from the side of the first coil layer 21a of the magnetic sensor 3b. The second wire 5a forms the first drive coil 5 as a planer coil.

Difference between the second coil layer 23a and the second coil layer 23b lies in the winding direction of the wires. In the second coil layer 23a, the third wire 6a is patterned so that the radius of the spiral with a terminal 6b as a start point increases in the anticlockwise direction when viewing from the side of the first coil layer 21a of the magnetic sensor 3b. The third wire 6a forms the reference coil 6 as a planer coil. The fourth wire 7a is patterned so that the radius of the spiral with a terminal 7b as a start point increases in the anticlockwise direction when viewing from the side of the first coil layer 21a of the magnetic sensor 3b. The fourth wire 7a forms the second drive coil 7 as a planer coil.

On the other hand, in the second coil layer 23b, the third wire 6a is patterned so that the radius of the spiral with a terminal 6b as a start point increases in the clockwise direction when viewing from the side of the first coil layer 21a of the magnetic sensor 3b. The third wire 6a forms the reference coil 6 as a planer coil. The fourth wire 7a is patterned so that the radius of the spiral with a terminal 7b as a start point increases in the clockwise direction when viewing from the side of the first coil layer 21a of the magnetic sensor 3b. The fourth wire 7a forms the second drive coil 7 as a planer coil.

The first drive coils 5 in the first coil layers 21a, 21b are electrically connected together in a unicursal manner so that the directions of the drive current flowing in the respective first drive coils 5 are the same. In order to achieve this configuration, the terminal 5b of the first drive coil 5 in the first coil layer 21a and the terminal 5b of the first drive coil 5 in the first coil layer 21b are electrically connected together through a connection plug 27g formed to pass through the upper insulating film 25a.

The detection coils 4 in the first coil layers 21a, 21b are electrically connected together in a unicursal manner so that the directions of the induced current flowing in the respective detection coils 4 are the same. In order to achieve this configuration, the terminal 4b of the detection coil 4 in the first coil layer 21a and the terminal 4b of the detection coil 4 in the first coil layer 21b are electrically connected together through a connection plug 27h formed to pass through the upper insulating film 25a.

The second drive coils 7 in the second coil layers 23a, 23b are electrically connected together in a unicursal manner so that the directions of the drive current flowing in the respective second drive coils 7 are the same. In order to achieve this configuration, the terminal 7b of the second drive coil 7 in the second coil layer 23a and the terminal 7b of the second drive coil 7 in the second coil layer 23b are electrically connected together through a connection plug 27i formed to pass through the lower insulating film 25c.

The reference coils 6 in the second coil layers 23a, 23b are electrically connected together in a unicursal manner so that the directions of the induced current flowing in the respective reference coils 6 are the same. In order to achieve this configuration, the terminal 6b of the reference coil 6 in the second coil layer 23a and the terminal 6b of the reference coil 6 in the second coil layer 23b are electrically connected together through a connection plug 27j formed to pass through the lower insulating film 25c.

The terminal 5c of the first drive coil 5 in the first coil layer 21b is located in the exterior of the first drive coil 5. The terminal 7c of the second drive coil 7 in the second coil layer 23a is located in the exterior of the second drive coil 7. The terminal 5c and the terminal 7c are electrically connected together through a connection plug 27k formed to pass through the intermediate insulating film 25b and the lower insulating film 25c. This makes the direction of the drive current flowing in the first drive coils 5 to be the same as the direction of the drive current flowing in the second drive coils 7.

The terminal 4c of the detection coil 4 in the first coil layer 21b is located in the exterior of the detection coil 4. The terminal 6c located in the exterior of the reference coil 6 in the second coil layer 23b is located in the exterior of the reference coil 6. The terminal 4c and the terminal 6c are electrically connected together through a connection plug 27l formed to pass through the intermediate insulating film 25b. This makes the direction of the induced current flowing in the detection coils 4 to be reverse to the direction of the induced current flowing in the reference coils 6.

According to the second embodiment, the two first coil layers and the two second coil layers (the first coil layers 21a, 21b and the second coil layers 23a, 23B) are provided. Thus, the output of the magnetic sensor 3b can be increased without increasing the area of the magnetic sensor 3b.

Further, according to the second embodiment, magnitude dispersion in the outputs of a plurality of the magnetic sensors 3b can be reduced. This advantage will be described in detail with reference to FIG. 10.

FIGS. 10A and 10B are diagrams showing examples of cross sections of the differential transformer type magnetic sensor 3b according to the second embodiment in a state where coil formed positions are displaced. FIG. 10A shows an example where formed positions of the detection coil 4 and the first drive coil 5 in the first coil layer 21a are displaced.

FIG. 10B shows an example where formed positions of the detection coil 4 and the first drive coil 5 in the first coil layer 21b are displaced.

Through the respective detection coils 4 in the second embodiment, magnetic fluxes pass, which are generated by the drive current flowing in the first drive coil 5 in the same layer and the drive current flowing in the first drive coil 5 in the other layer. In the case shown in FIG. 10A, the amount of the magnetic flux generated by the drive current flowing in the first drive coil 5 in the first coil layer 21b, of which formed position is not displaced, decreases in the detection coil 4 in the first coil layer 21a, of which formed position is displaced.

However, as has been described in the first embodiment, the amount of the magnetic flux generated by the drive current flowing in the first drive coil 5 in the first coil layer 21a, of which formed position is displaced, will not vary in the detection coil 4 in the same layer (the first coil layer 21a). Accordingly, in the absence of the detection target, the difference between the amount of the magnetic fluxes passing through the detection coils 4 and the amount of the magnetic fluxes passing through the reference coils 6 can be reduced when compared with the case where only the formed position of the detection coil 4 or the first drive coil 5 is displaced as in Comparative Example shown in FIGS. 7A and 7B. The same can be applied to the case where the formed positions of the detection coil 4 and the first drive coil 5 in the first coil layer 21b are displaced as shown in FIG. 10B.

The same can be applied also to the reference coils 6 as the detection coils 4. Through the respective reference coils 6, magnetic fluxes pass, which are generated by the drive current flowing in the second drive coil 7 in the same layer and the drive current flowing in the second drive coil 7 in the other layer. Although not shown, the case where the formed positions of the reference coil 6 and the second drive coil 7 in the second coil layer 23a are displaced will be described, for example. The amount of the magnetic flux generated by the drive current flowing in the second drive coil 7 in the second coil layer 23b, of which formed position is not displaced, decreases in the reference coil 6 in the second coil layer 23a.

However, similarly to the above described first embodiment, the amount of the magnetic flux generated by the drive current flowing in the second drive coil 7 in the second coil layer 23a will not vary in the reference coil 6 in the same layer (the second coil layer 23a). Accordingly, in the absence of the detection target, the difference between the amount of the magnetic fluxes passing through the detection coils 4 and the amount of the magnetic fluxes passing through the reference coils 6 can be reduced when compared with the case where only the formed position of the reference coil 6 or the second drive coil 7 is displaced.

As described above, according to the second embodiment, where the formed position of any of the detection coils 4, the first drive coils 5, the reference coils 6, and the second drive coils 7 as planer coils is displaced, the difference between the amount of the magnetic fluxes passing through the detection coils 4 and the amount of the magnetic fluxes passing through the reference coils 6 in the absence of the detection target can be reduced. Thus, magnitude dispersion in the outputs the differential transformer type magnetic sensors 3b can be reduced.

Figure 11:
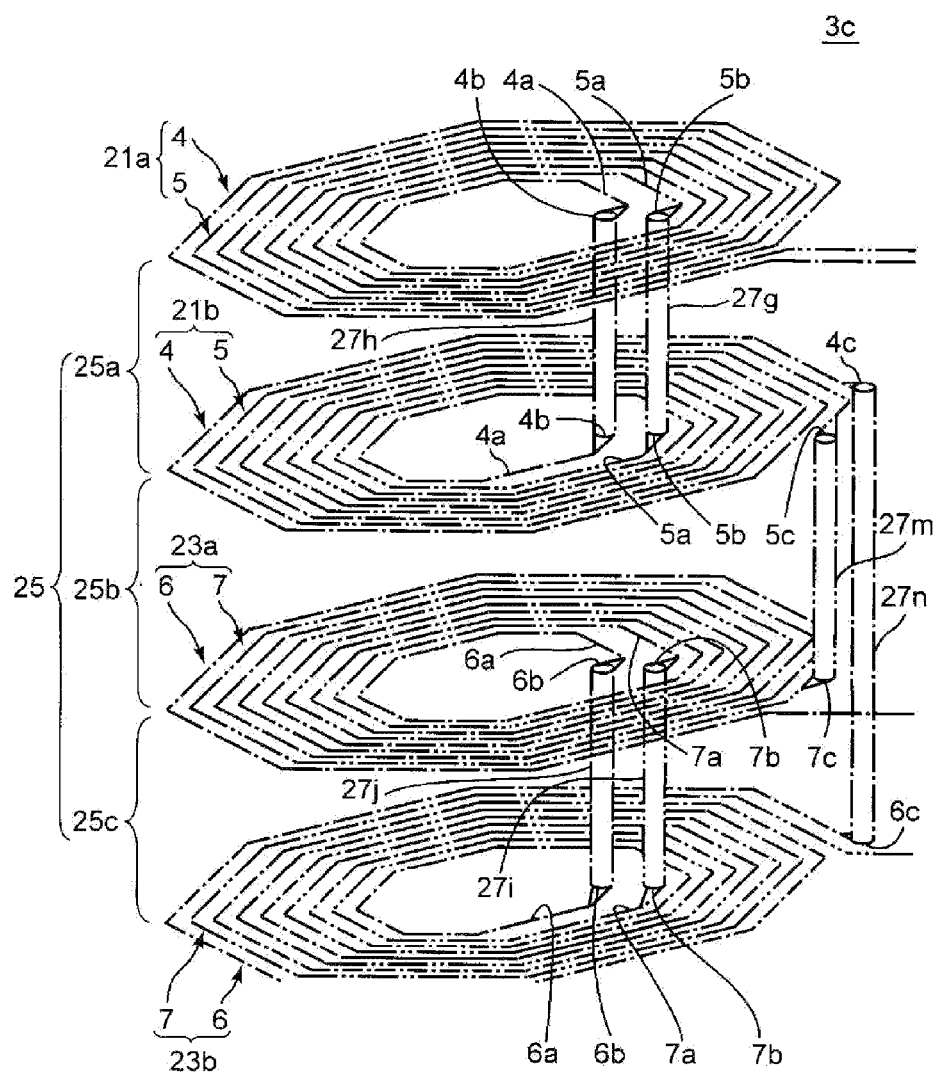
FIG. 11 is a perspective view showing a configuration of a differential transformer type magnetic sensor according to a modified example of the second embodiment.

A modified example of the second embodiment will now be described herein with reference to FIG. 11. FIG. 11 is a perspective view showing a configuration of a differential transformer type magnetic sensor 3c according to the modified example of the second embodiment. Difference of the magnetic sensor 3c from the magnetic sensor 3b according to the second embodiment shown in FIG. 9 lies in that the positions of the second coil layer 23a and the second coil layer 23b are reverse.

The terminal 5c of the first drive coil 5 in the first coil layer 21b and the terminal 7c of the second drive coil 7 in the second coil layer 23a are electrically connected together through a connection plug 27m formed to pass through the intermediate insulating film 25b. This makes the direction of the drive current flowing in the first drive coils 5 to be the same as the direction of the drive current flowing in the second drive coils 7.

The terminal 4c of the detection coil 4 in the first coil layer 21b and the terminal 6c of the reference coil 6 in the second coil layer 23b are electrically connected together through a connection plug 27n formed to pass through the intermediate insulating film 25b and the lower insulating film 25c. This makes the direction of the induced current flowing in the detection coils 4 to be reverse to the direction of the induced current flowing in the reference coils 6.

As described above, in the modified example, by changing the connection between the respective first drive coils 5 and the respective second drive coils 7 in the magnetic sensor 3b according to the second embodiment, the direction of the drive current flowing in the first drive coils 5 is made to be the same as the direction of the drive current flowing in the second drive coils 7.

Similarly, in the modified example, by changing the connection between the respective detection coils 4 and the respective reference coils 6 in the magnetic sensor 3b according to the second embodiment, the direction of the induced current flowing in the detection coils 4 is made to be reverse to the direction of the induced current flowing in the reference coils 6.

The magnetic sensor 3c according to the modified example can offer the same advantages as the magnetic sensor 3b according to the second embodiment.

What is claimed is:

1. A differential transformer type magnetic sensor, comprising:
    a first coil layer including a detection coil formed of a single planospiral first wire located on a plane and a first drive coil formed of a single planospiral second wire running in parallel to the first wire on the same plane as the first wire;
    a second coil layer including a reference coil formed of a single planospiral third wire located on another plane and a second drive coil formed of a single planospiral fourth wire running in parallel to the third wire on the same plane as the third wire; and
    a first insulating layer arranged between the first coil layer and the second coil layer,
    wherein the single first wire is wound plural times around a center continuously to have a first spiral structure,
    the single second wire is wound plural times around the center continuously to have a second spiral structure,
    at least a part of the second spiral structure is disposed between an outermost peripheral part and an innermost peripheral part of the first spiral structure,
    the single third wire is wound plural times around another center continuously to have a third spiral structure,
    the single fourth wire is wound plural times around the other center continuously to have a fourth spiral structure,
    at least a part of the fourth spiral structure is disposed between an outermost peripheral part and an innermost peripheral part of the third spiral structure,
    the first drive coil and the second drive coil are electrically connected together so that a direction of drive current flowing in the first drive coil is the same as a direction of drive current flowing in the second drive coil, and
    the detection coil and the reference coil are electrically connected together so that a direction of induced current flowing in the detection coil is reverse to a direction of induced current flowing in the reference coil.

2. A differential transformer type magnetic sensor comprising:
    a first coil layer including a detection coil formed of a planospiral first wire located on a plane and a first drive coil formed of a planospiral second wire running in parallel to the first wire on the same plane as the first wire;
    a second coil layer including a reference coil formed of a planospiral third wire located on a plane and a second drive coil formed of a planospiral fourth wire running in parallel to the third wire on the same plane as the third wire; and
    a first insulating layer arranged between the first coil layer and the second coil layer, wherein
    the first drive coil and the second drive coil are electrically connected together so that a direction of drive current flowing in the first drive coil is the same as a direction of drive current flowing in the second drive coil, and
    the detection coil and the reference coil are electrically connected together so that a direction of induced current flowing in the detection coil is reverse to a direction of induced current flowing in the reference coil,
    the first coil layer includes a plurality of first coil layer, while the second coil layer includes a plurality of second coil layers, the number of the first coil layers being equal to the number of the second coil layers,
    the differential transformer type magnetic sensor further comprising:
    a second insulating layer interposed between two first coil layers of the plurality of first coil layers on a side of one of surfaces of the first insulating layer; and
    a third insulating layer interposed between two second coil layers of the plurality of second coil layers on a side of the other surface of the first insulating layer,
    wherein respective first drive coils in the plurality of first coil layers are electrically connected together so that directions of drive current flowing in the respective first drive coils in the plurality of first coil layers are the same,
    respective second drive coils in the plurality of second coil layers are electrically connected together so that directions of drive current flowing in the respective second drive coils in the plurality of second coil layers are the same,
    respective detection coils in the plurality of first coil layers are electrically connected together so that directions of induced current flowing in the respective detection coils in the plurality of first coil layers are the same, and
    respective reference coils in the plurality of second coil layers are electrically connected together so that directions of induced current flowing in the respective reference coils in the plurality of second coil layers are the same.

3. A differential transformer type magnetic sensor according to claim 2, wherein
    each number of the plurality of first coil layers and the plurality of second coil layers is two, and
    one of the two first coil layers, the second insulating layer, the other of the two first coil layers, the first insulating layer, one of the two second coil layers, the third insulating layer, and the other of the two second coil layers are staked in this order.

4. An image forming apparatus, comprising a differential transformer type magnetic sensor, wherein the differential transformer type magnetic sensor includes:
- a first coil layer including a detection coil formed of a planospiral first wire located on a plane and a first drive coil formed of a planospiral second wire running in parallel to the first wire on the same plane as the first wire;
- a second coil layer including a reference coil formed of a planospiral third wire located on a plane and a second drive coil formed of a planospiral fourth wire running in parallel to the third wire on the same plane as the third wire; and
- a first insulating layer arranged between the first coil layer and the second coil layer, wherein the first drive coil and the second drive coil are electrically connected together so that a direction of drive current flowing in the first drive coil is the same as a direction of drive current flowing in the second drive coil, the detection coil and the reference coil are electrically connected together so that a direction of induced current flowing in the detection coil is reverse to a direction of induced current flowing in the reference coil, the image forming apparatus further comprises:

a photosensitive drum; and a developing section that supplies toner to the photosensitive drum, and the differential transformer magnetic sensor detects variation in height of a topmost part of the toner in the developing section.

\* \* \* \* \*